(12) United States Patent
Tsyplukhin

(10) Patent No.: US 11,963,776 B2
(45) Date of Patent: Apr. 23, 2024

(54) SYSTEM AND METHOD FOR BUILDING A MAGNETIC FIELD MAP

(71) Applicant: BROAD MIND INC., Claymont, DE (US)

(72) Inventor: Ivan Tsyplukhin, Moscow (RU)

(73) Assignee: BROAD MIND INC., Claymont, DE (US)

( * ) Notice: Subject to any disclaimer, the term of this patent is extended or adjusted under 35 U.S.C. 154(b) by 238 days.

(21) Appl. No.: 17/541,981

(22) Filed: Dec. 3, 2021

(65) Prior Publication Data
US 2022/0175290 A1 Jun. 9, 2022

Related U.S. Application Data

(60) Provisional application No. 63/121,301, filed on Dec. 4, 2020.

(51) Int. Cl.
*A61B 5/245* (2021.01)
*A61B 5/00* (2006.01)
*G01R 33/26* (2006.01)

(52) U.S. Cl.
CPC ............ *A61B 5/245* (2021.01); *A61B 5/0042* (2013.01); *G01R 33/26* (2013.01); *A61B 2562/0238* (2013.01); *A61B 2562/0242* (2013.01); *A61B 2562/182* (2013.01)

(58) Field of Classification Search
CPC .... A61B 2562/0238; A61B 2562/0242; A61B 2562/182; A61B 5/0042; A61B 5/245; G01R 33/26
See application file for complete search history.

(56) References Cited

U.S. PATENT DOCUMENTS

| 7,050,231 B2 * | 5/2006 | Matsushita | ............. G02F 1/093 385/11 |
| 2017/0234913 A1 * | 8/2017 | Yao | ...................... G01R 15/246 324/96 |

OTHER PUBLICATIONS

J.M. Hafez, , J. Gao, J.G. Eden, Detection of weak (similar to 0.5-300 nT), low frequency (5-100 Hz) magnetic fields at room temperature by kilohertz modulation of the magneto-optical hysteresis in rare earth-iron garnet films, Appl. Phys. Lett. 90 (2007) 13.
H. Watarai, P. Gangopadhyay, R. A. Norwood, and N. Peyghambarian, Total Internal Reflection Magneto-optical Detection of Dysprosium(III) Ions Adsorbed at Liquid-Liquid Interface, Chem. Lett. 43 (2014) 1651.
(Continued)

*Primary Examiner* — Jay Patidar
(74) *Attorney, Agent, or Firm* — Maschoff Brennan

(57) ABSTRACT

A measurement system is proposed for building a magnetic field map of an object. The system comprising: a light source arrangement for emitting a plurality of light beams, a respective light beam being configured to travel in the measurement system along a respective optical path; a plurality of measurement sensors sharing a first magneto-optical layer comprising at least a first Faraday material layer and a first light reflector for reflecting the plurality of light beams travelled through the first Faraday material layer in a first direction back to the first Faraday material layer in a second, opposite direction; one or more reference sensors; and one or more light detectors.

19 Claims, 4 Drawing Sheets

(56) References Cited

OTHER PUBLICATIONS

B. Amirsolaimani, P. Gangopadhyay, A.P. Persoons, S.A. Showghi, L.J. LaComb, R.A. Norwood, N. Peyghambarian, High sensitivity magnetometer using nanocomposite polymers with large magneto-optic response, Optics Letters 43 (2018) 4615.

A. Lopez Santiago, Magneto-optical polymer and devices, PhD dissertation (2014).

M.E. Mackay et al., General strategies for nanoparticle dispersion. Science 311 (2006) 1740.

D.A. Smith et al., Magneto-optical spectra of closely spaced magnetite nanoparticles, Journal of Applied Physics 97 (2005) 10M504.

S. Xu, S.M. Rochester, V.V. Yashchuk, M.H. Donaldson, D. Budker, Construction and applications of an atomic magnetic gradiometer based on nonlinear magneto-optical rotation. Rev. Sci. Instr. 77, 083106 (2006).

Amirsolaimani, et al., "High sensitivity magnetometer using nanocomposite polymers with large magneto-optic response", Optics Letters, vol. 43, No. 19, 2018, pp. 4615-4618.

Boto, et al., "A new generation of magnetoencephalography: Room temperature measurements using optically-pumped magnetometers", NeuroImage 149, www.elsevier.com/locate/neuroimage, 2017, pp. 404-414.

Budker, et al., "Optical Magnetometry", Cambridge University Press, 978-1-107-01035-2, 2013, 17 pgs.

Lopez-Santiago, et al., "Faraday rotation in magnetite-polymethylmethacrylate core-shell nanocomposites with high optical quality", Applied Physics Letters 95, 2009, 4 pgs.

Miyamoto, et al., "Effective Transition Probability for the Faraday Effect of Lanthanide(III) Ion Solutions", JACS Communications, 2009, pp. 6328-6329.

Tantaswadi, et al., "All-fiber, in-line Sagnac magnetometer", SPIE vol. 3580, pp. 118-122.

Tsuji-Lio, et al., "Fiberoptic heterodyne magnetic field sensor for long-pulsed fusion devices". Review of Scientific Instruments, vol. 72, No. 1, 2001, 5 pgs.

* cited by examiner

SYSTEM AND METHOD FOR BUILDING A MAGNETIC FIELD MAP

TECHNICAL FIELD

The present disclosure pertains to a novel device for recording magnetic fields produced by electric currents occurring naturally in an object, such as a human or animal brain and related to neural activity. The invention equally relates to a method of recording magnetic fields with such a device.

BACKGROUND OF THE INVENTION

Magnetoencephalography (MEG) is a functional neuroimaging technique for mapping brain activity by recording magnetic fields produced by electric currents occurring naturally in the brain. Currently available devices use a system of very sensitive magnetometers to record magnetic fields produced by neural activity in the brain.

Today most of the MEG devices are superconducting quantum interference devices (SQUIDs). MEG devices based on arrays of SQUIDs require a magnetically shielded room, while sensors of the SQUIDs inside the device require cooling with liquid helium. These requirements make SQUID-based MEG solutions expensive and impossible to use in a normal environment.

An emerging type of magnetometers called optically pumped magnetometers (OPMs) were recently applied for MEG. Optically pumped magnetometers are magnetometers based on a spin exchange relaxation-free (SERF) regime. The vapor cell inside these types of magnetometers requires heating, but the whole sensor is able to operate at room temperature. This allows the sensors to be placed closer to the scull (head), compared to SQUID arrays, which is good for MEG applications. The price of an individual OPM sensor is lower than the price of a SQUID sensor, but the SERF regime and the OPM sensor itself still require a magnetically shielded room to operate.

There exist also magnetic field sensors based on the Faraday effect (Faraday rotation) in a medium or film, but they are not modified for high density MEG applications. The operating principle is to measure the deflection angle of the polarization vector of linearly polarized light after passing a medium in a magnetic field B. The deflection angle or polarization rotation angle is the angle between the starting and ending polarizations. The deflection angle is linearly related to the magnitude of the magnetic field through the Verdet constant V (deflection angle=V×B). The Verdet constant is an optical property describing the strength of the Faraday effect for a particular material. The Verdet constant of a material is typically wavelength dependent. At present an intensive study of materials with the high Verdet constant is continued.

SUMMARY OF THE INVENTION

It is an object of the present invention to overcome at least some of the problems identified above related to magnetoencephalography devices. More specifically, one of the aims of the present invention is to provide a magnetoencephalography device that is based on the Faraday effect.

According to a first aspect of the invention, there is provided a measurement system for determining a magnetic field map of an object as recited in claim 1.

The present invention thus proposes a novel system of magnetometers (i.e. sensors or detectors), based on the Faraday effect that is able to operate in a regular environment, without a magnetically shielded room and with a built-in sensor for continuous calibration. This approach allows us to apply the proposed system not only for functional neuroimaging, but also to implement it as a reading (recording) system for brain activity, to use it to further interpret signals present in the system, and to use it for applications like brain-computer interface.

The proposed approach greatly simplifies and reduces the costs of the magnetometers in comparison to SQUID and OPM magnetometers. Magnetometers based on the Faraday effect use special Faraday materials, and they do not use the SERF regime, as opposed to OPMs, and they can thus operate in a non-zero external magnetic field, out of a magnetically shielded room. Applying a high Verdet constant material (HVCM), with the Verdet constant approximately equal to $10^8°/Tm$ or higher, like nanocomposite polymer films or other materials with a high Verdet constant, we can achieve a very high sensitivity with this type of sensor (up to 15 fT/sqrtHz).

The proposed system can also form a system of high-density magnetometers for MEG and brain-computer interfaces. It can be used as a single sensor pack, to record magnetic fields produced by brain activity in a specific region or as a system of sensor packs for traditional MEG. The main advantages of the present invention are the following: high-density measurements of the magnetic field, and the ability to function without a magnetically shielded room enabled by an in-built calibration sensor for continued calibration. These advantages are important for magnetoencephalography, and applications related to brain-computer interfaces.

According to the present invention, a given sensor module comprises one common Faraday material film for a plurality of optical fibers (or light beams), and thus a large number of magnetometers (sensors) can be provided within one module. The maximum density of the sensors in the proposed system is limited by the size of the light beam, and it's an order of magnitude greater than with systems based on OPMs.

In addition, the present invention allows the point where the magnetic field is measured to be very close to a scalp, which increases the accuracy of the measurements for MEG and for other applications.

According to a second aspect of the invention, there is provided a method of determining a magnetic field map by using the measurement system according to the first aspect.

Other aspects of the invention are recited in the dependent claims attached hereto.

BRIEF DESCRIPTION OF THE DRAWINGS

Other features and advantages of the invention will become apparent from the following description of a non-limiting example embodiment, with reference to the appended drawings, in which.

DETAILED DESCRIPTION OF AN EMBODIMENT OF THE INVENTION

Figure 1:
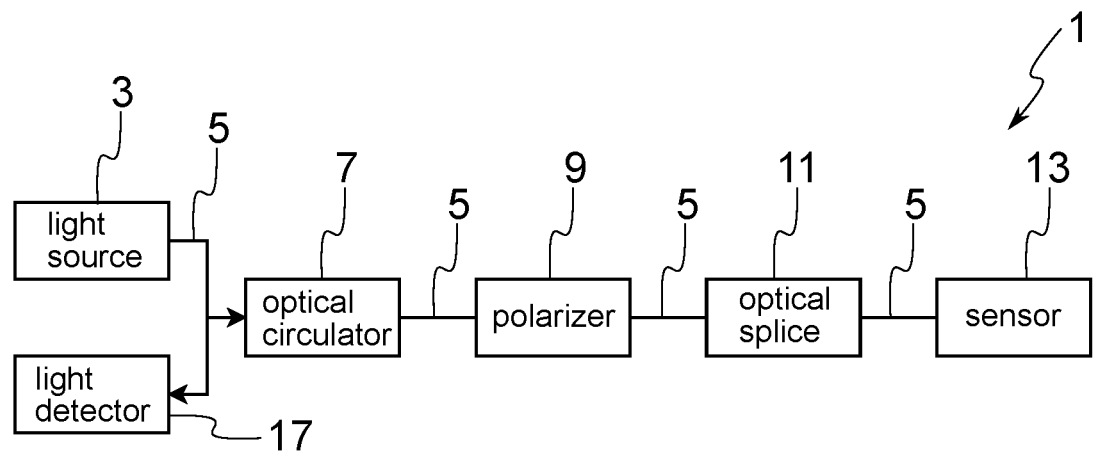
FIG. 1 shows a magnetometer with an in-line Sagnac interferometer-like optical path that may be used in the measurement system according to the present invention.

An embodiment of the present invention will now be described in detail with reference to the attached figures. The embodiment is described in the context of an optical system based on the Sagnac effect (interferometer), but the teachings of the invention are not limited to this environment. For instance, other optical systems could be used instead. Identical or corresponding functional and structural elements which appear in the different drawings are assigned the same reference numerals. It is to be noted that the use of words "first", "second" and "third", etc. may not imply any kind of particular order or hierarchy unless this is explicitly or implicitly made clear in the context. As becomes clear by reading the following description, the proposed novel system dramatically reduces the cost of an MEG system compared to existing solutions. First of the advantages of the system we represent, is the ability to arrange a large number of sensors very densely. The second main advantage is the ability to operate out of a magnetically shielded room, because of a built-in calibration sensor.

FIG. 1 illustrates an optical system 1 based on the Sagnac effect. As can be seen, a light source 3, which in this example is a laser source, is provided to generate and emit one or more light or optical signals, which in this case are light beams. The word signal in the present description is to be understood broadly. In particular, the word signal does not imply that any kind of information is necessarily encoded in the signal. The light beam is understood to travel along an optical path between different elements in the system. In the present example, the generated light beam travels through an optical fiber 5, which in the present case is a polarization-maintaining optical fiber connecting different elements of the system as described in the following. However, it is to be noted that the optical fiber is an optional feature in the present invention. From the light source 3 the light beam is configured to enter an optical circulator 7. An optical circulator is typically a three- or four-port optical device designed such that light entering any port exits from the next. This means that if light enters port 1, it is emitted from port 2, but if some of the emitted light is reflected back to the circulator, it exits the circulator from port 3. The light beam is next arranged to enter a polarizer 9, which is configured to convert the light beam to a linearly polarized light beam. A polarizer is an optical filter that lets light waves of a specific polarization pass through while blocking light waves of other polarizations. It can thus filter a beam of light of undefined or mixed polarization into a beam of well-defined polarization, which is a polarized light beam. The light beam is next arranged to enter an optical splice 11, which in this example is a 45-degree splice, configured to split the polarized light into two different polarizations, in this case orthogonal x and y polarizations, and to combine the back-reflected orthogonal polarizations from a sensor 13. This combination creates an interference pattern related to the Faraday rotation inside a magneto-optical element, layer or film 15. The interference pattern caused by the phase shift between the two polarizations induced by a magnetic field is detected using a balanced light detector 17, which in this case is a photodiode. The light beam with the two orthogonal polarizations is thus arranged to enter the sensor or detector 13, which is better illustrated in FIG. 2. It is to be noted that depending on how the optical system is defined, the light source 3 and the sensor 13 may not be considered to be part of the optical system 1.

Figure 2:
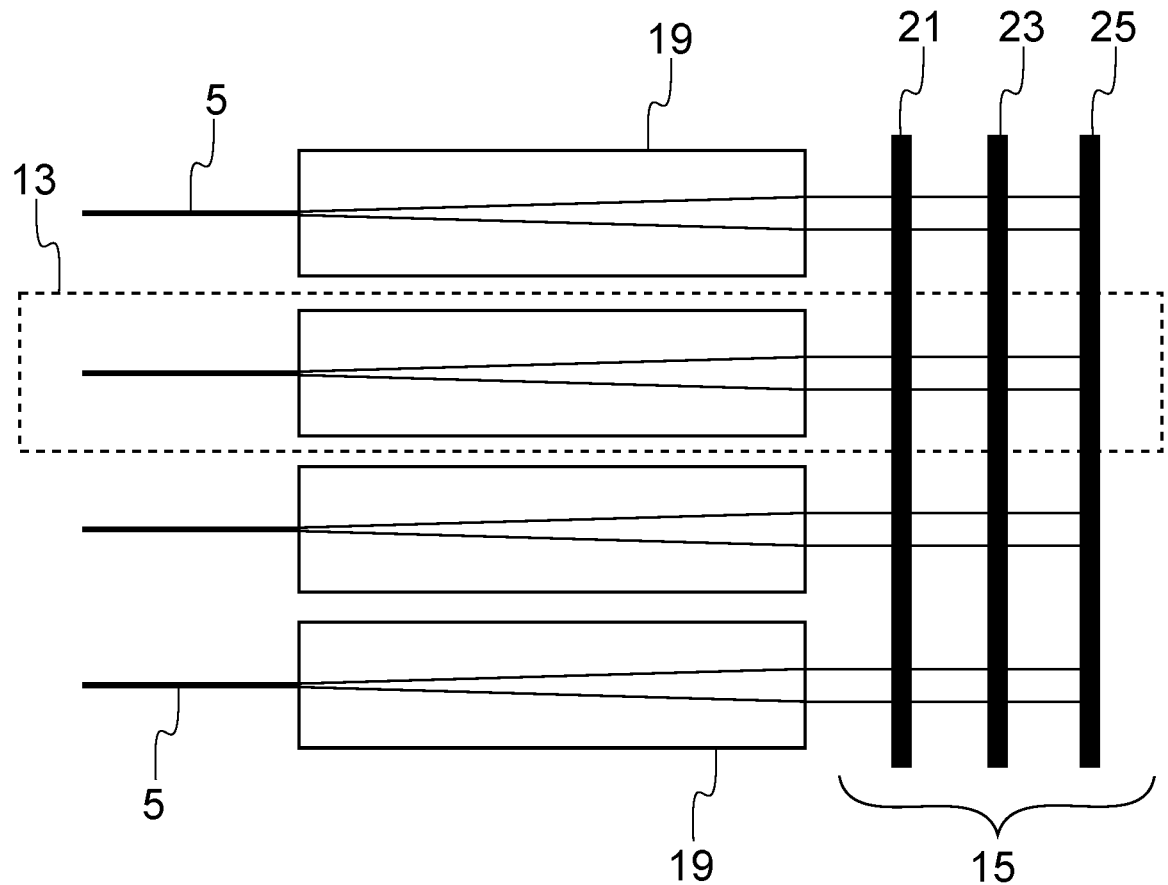
FIG. 2 illustrates the principle of sharing a single magneto-optical film between a plurality of optical fibers according to the teachings of the present invention.

FIG. 2 shows four sensors 13, which are also referred to as measurement sensors. One end of the fibers may or may not be considered to be part of the respective sensor. The light exiting the respective fiber is arranged to be fed into a collimator 19, which is a device configured to narrow a beam of particles or waves. This can mean either to cause the directions of motion to become more aligned in a specific direction (i.e., make collimated light or parallel rays), or to cause the spatial cross section of the beam to become smaller (beam limiting device). A common single magneto-optical film or layer 15 is provided and shared between a plurality of sensors or optical fibers or more broadly between a plurality of light beams. A material can be understood to be magneto-optical (MO) if it affects the propagation characteristics of light when an external magnetic field is applied to it. The magneto-optical film 15 in this example comprises a quarter-wave plate 21 ($\lambda/4$), which is configured to turn linearly polarized light into circularly polarized light and vice versa. To do this, the waveplate should advantageously be oriented so that equal amounts of fast and slow waves are excited. Next in the light path, the magneto-optical film comprises a Faraday material layer or film 23 that is configured to create a phase shift between the two circular polarizations (that were orthogonal before passing the quarter-wave plate 21 directly) inside the magneto-optical material or media of the magneto-optical film 15. The Faraday material has advantageously a high Verdet constant. Such materials include inorganic rare-earth materials, such as yttrium iron garnet, $Tb^{+3}$ doped paramagnetic glass, and gallium gadolinium garnet under noncryogenic conditions. Cobalt-zinc (Co—Zn) ferrite thin films (with thickness between 60 nm and 180 nm) may also be used having the Verdet constant of approximately $4.6 \times 10^{7 \circ}/Tm$, or bismuth-dysprosium (Bi—Dy) ferrite garnet films having a maximum Verdet constant of approximately $7.5 \times 10^{6 \circ}/Tm$. In addition to inorganic compounds, the so-called chiral hydrocarbon polymers, which have a high Verdet constant, may also be used as the Faraday material. Yet another option is to use synthesized polymer matrices with embedded magnetite nanoparticles. The values of the Verdet constant in these kinds of films reach approximately $3.2 \times 10^{8 \circ}/Tm$. This would allow the magnetic field to be measured with the sensitivity of 20 $fT/Hz^{1/2}$.

A light reflector 25 is provided to reflect the light beam exiting the Faraday material film 23 back to the Faraday material film and thus towards the light detector 17. It is to be noted that the different layers of the magneto-optical element may be in direct contact with each other, instead of having a given spacing between them as shown in FIG. 2. The magneto-optical film thus implements a physical magneto-optical phenomenon called Faraday effect or Faraday rotation, sometimes referred to as the magneto-optic Faraday effect (MOFE). The Faraday effect causes a polarization rotation of light which is proportional to the projection of the magnetic field along the direction of the light propagation. It can be considered as a special case of gyroelectromagnetism obtained when the dielectric permittivity tensor is diagonal. The Faraday effect occurs in most optically transparent dielectric materials (including liquids) under the influence of magnetic fields. This effect is caused by left and right circularly polarized waves propagating at slightly different speeds, a property known as circular birefringence. As a linear polarization can be decomposed into the superposition of two equal-amplitude circularly polarized components of opposite handedness and different phase, the effect of a relative phase shift, induced by the Faraday effect, is to rotate the orientation of a wave's linear polarization.

Figure 3:
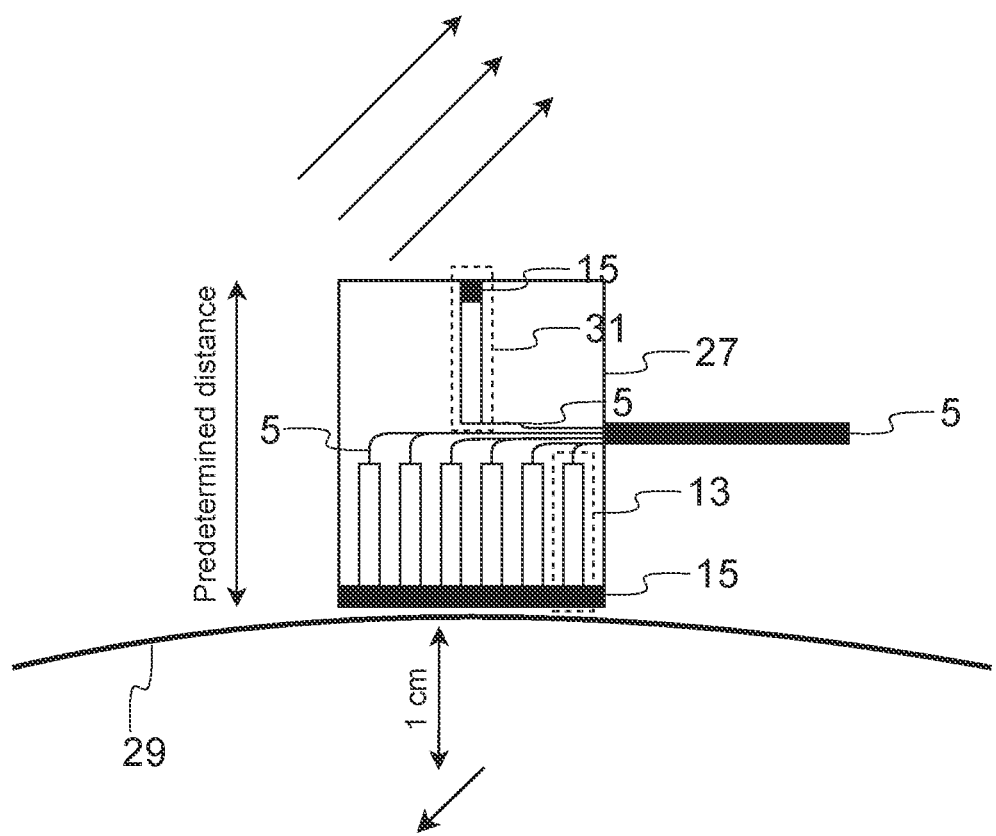
FIG. 3 illustrates an all-optic sensor pack arrangement with a plurality of measurement sensors comprising a first single magneto-optical film and a reference sensor comprising a second single magneto-optical film.

FIG. 3 shows the placement of a sensor module or sensor pack 27 on the scalp 29 of a person. As can be seen, the sensor module comprises a plurality of measurement sensors 13, as well as one or more reference sensors 31 or detectors for measuring an external magnetic field, which may then be taken into account when determining the magnetic field map of the brain. The reference sensor(s) is/are in this example identical or substantially identical to the measurement sensors 13, and thus in the present example they have their own collimator 19 and magneto-optical film 15. One optical fiber per sensor is provided so that the plurality of optical fibers form a fiber bundle. The reference sensor(s) is/are placed a given (known predetermined) distance from the measurement sensors 13. It is to be noted that the distances given in FIG. 3 are merely example values but any other suitable predetermined distances may be used instead. Three parallel arrows outside the brain in FIG. 3 illustrate the external magnetic field, while the arrow in the brain in FIG. 3 illustrates the direction of the local brain current.

Figure 4:
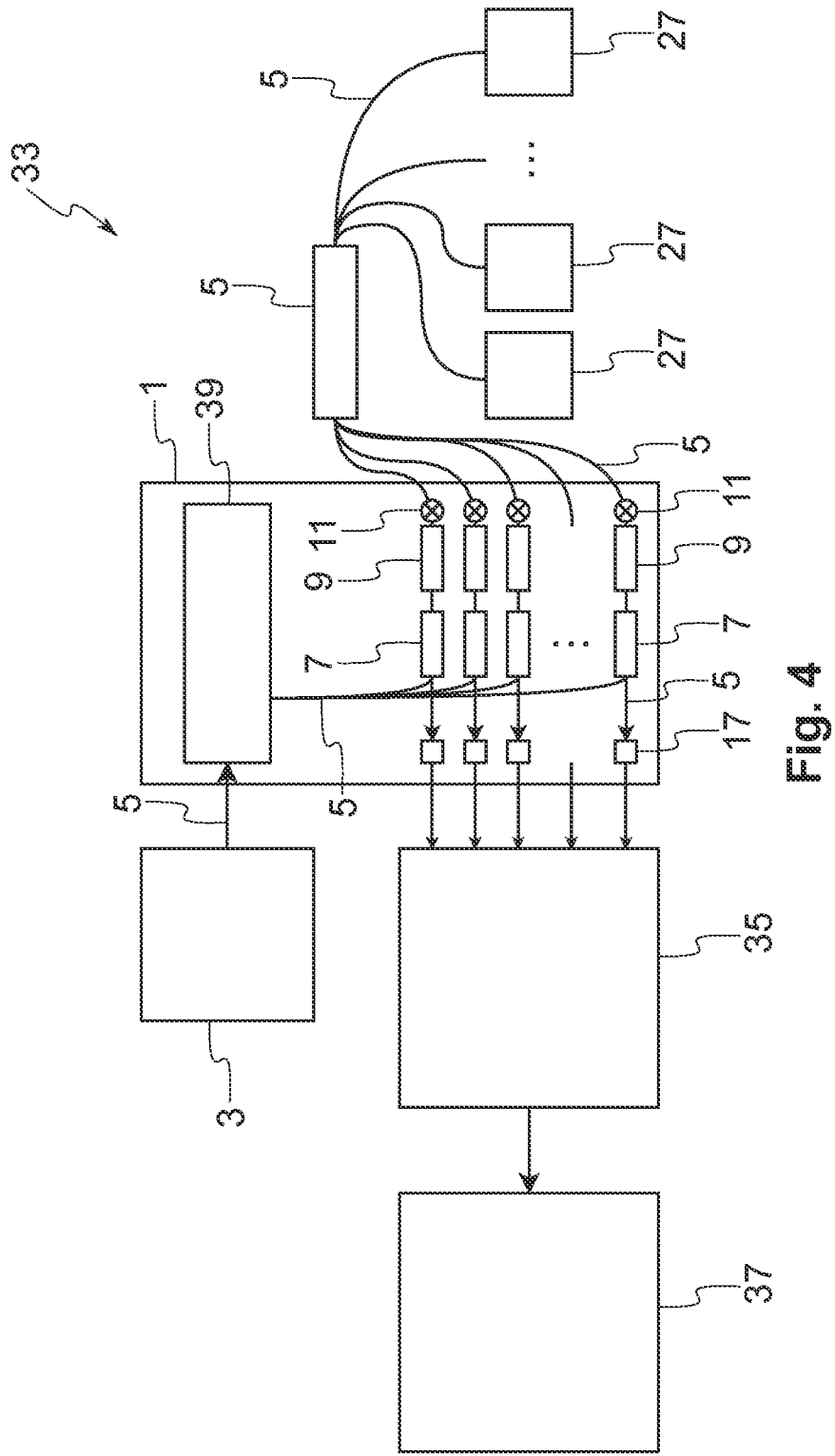
FIG. 4 illustrates a complete measurement system according to an example of the present invention.

FIG. 4 shows a complete measurement system 33 according to one example, which also illustrates the connection scheme of the sensors. The general design can be understood to be divided into several sub-systems or sub-components: a laser system comprising the laser source 3 that generates light; an optical system 1 that distributes light and registers a signal; sensor modules 27 or detector systems, as well as a digitization system 35 and a data analysis system 37. Light is excited by the laser system 3 and enters the optical system 1. In the present example, the optical system comprises photodiodes 17, one or more fiber-optic splitters 39 (also known as beam splitters), circulators 7, polarizers 9 and optical splices 11. Laser light is divided here by the splitter into several beams. The beams fall on the circulator and propagate in the optical system according to the Sagnac scheme as described above. The right part of FIG. 4 shows sensor modules 27 or sensor packs with several measurement sensors and only one common magneto-optical film 15 for measuring the brain field, as well as an external magnetic field sensor(s) 31 with another magneto-optical film, i.e., the reference sensor. The signals from the sensors are recorded in the optical system 1, digitized by an analog-to-digital converter of the digitization system 35, and transmitted to the data analysis system 37. Signal processing involves mainly extracting noise associated with an external magnetic field, as well as taking into account the drift of the signal from the laser.

The operation of the measurement system 33 and the advantages of the present invention are next explained in more detail. By using one magneto-optical material 15 (i.e., the magneto-optical film) for several optical fibers (fibers could be replaced with light beams or a crystal structure) within one sensor module 27, the density of the measurements (recordings) can be dramatically increased. The number of optical fibers or light beams at a given time instant equals the number of sensors. With this approach the density of the sensors is limited by the diameter of the perpendicular incident light beam and the wavelength (a characteristic value of less than 1 mm). For comparison, the density of the systems based on optical pump magnetometers is limited by the diffusion of alkali atoms in the gas and is currently approximately 1 mm.

The use of the optical fibers 5 simplifies the supply of the light beams to the magneto-optical film 15. As mentioned above, the optical system 1 is in the present example based on the Sagnac scheme as described for instance in a publication by P. Tantaswadi, J. Blake, "All-fiber in-line Sagnac magnetometer," Proceedings of the SPIE 3580 (1998) 118. FIG. 1 shows an example Sagnac scheme adapted to detect the Faraday effect in a thin film. In the present example, the thickness of this film is in the range of 100 μm to 500 μm. This scheme allows all the electronic components to be removed from the film by keeping a small element, forming the sensor 13. FIG. 2 illustrates the concept of installing several sensors 13 with only one common magneto-optical film 15. The sensor in this case includes an end of an optical fiber 5, the collimating lens (collimator) 19, and the magneto-optical film 15 containing the quarter-wave layer 21, the Faraday material layer 23 and the mirror coating 25.

The Sagnac scheme operates as follows. The laser signal passes through the circulator 7 and enters the polarizer 9. Next, the light enters the optical splice 11 which splits the polarization into two components along the horizontal and vertical axes of the polarization-maintaining optical fiber 5. After having passed the main part of the optical path inside the optical fiber it propagates through the collimator 19 and exits the collimator 19, now travelling without optical fiber into the quarter-wave plate 21. The quarter-wave plate converts the two orthogonal polarizations into right-handed and left-handed circular polarizations. The reflective surface (such as a metal surface) behind the Faraday material 23 acts as a mirror that reverses the polarization thereby introducing a π-phase shift. The reflected light passes through the Faraday material and the quarter-wave plate in an opposite direction, and the light with the given polarization that passed in a first direction through the optical fiber 5 now moves in a second direction. Then the light passing through the optical fiber, the optical splice, the polarizer, and the circulator enters the photodiode.

A given light beam passes through the polarizer 9, the optical fiber 5, the quarter-wave plate 21, the Faraday material 23, and is reflected at the mirror 25, before passing again through the Faraday material 23, the quarter-wave plate 21, the optical fiber 5, and the polarizer 9. The Faraday effect creates a phase shift between the two orthogonal polarizations inside the magneto-optical material 15. The system design and double pass through the film increase the phase difference caused by the Faraday effect. In view of the above, in the present example, the measurement and reference sensors are quantum sensors due to the underlying quantum effects being present in the artificially engineered magneto-optical material.

The polarization-maintaining optical fiber 5 is the main part of the optical path of the light beam (the other part being inside the sensor). The light beam acquires different phases along the different axes here. The main contribution of the Sagnac interferometer is the reverse movement of light along the same fiber. Due to the passage of twice through the magneto-optical film and reflection, the wave, which initially traveled along the horizontal axis, will return along the vertical. Thus, the returning waves acquire the same phase in the optical fiber. As a result, this scheme makes it possible to reduce the influence of mechanical vibrations, linear and circular birefringence, and changes in fiber length due to fluctuations in ambient temperature, mechanical stresses, bends, and the Earth's magnetic field.

Figure 5C:
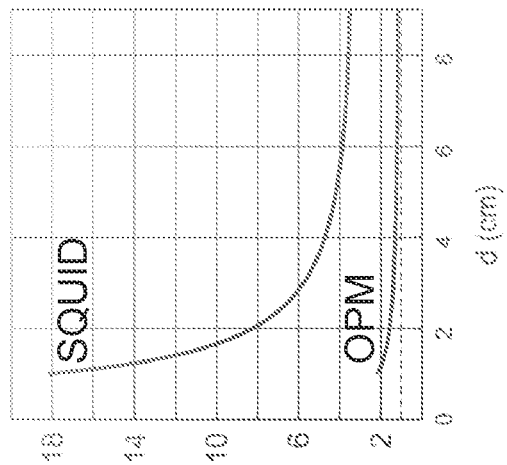
FIG. 5c is a diagram showing the ratio of magnetic fields measured by the proposed Faraday material-based measurement system and an OPM-based measurement system on the one hand, and the proposed Faraday material-based measurement system and a SQUID-based measurement system on the other hand as a function of depth.
Figure 5B:
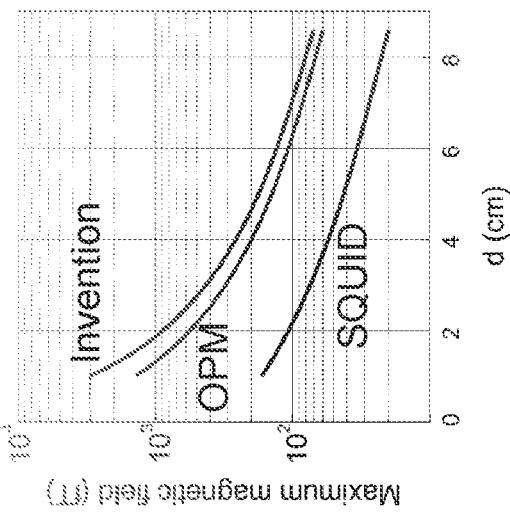
FIG. 5b is a diagram showing the magnitude of the measured radial magnetic field as a function of source depth for the proposed Faraday material-based measurement system, a SQUID-based measurement system, and, and an OPM-based measurement system.
Figure 5A:
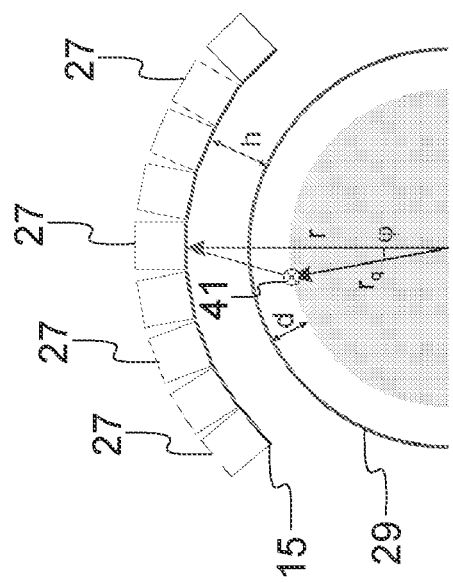
FIG. 5a illustrates a schematic of an analytical model for assessing signal magnitude as a function of source depth.

The second main advantage of the present invention is the ability to operate in a wide temperature range including room temperatures +15-+25 degrees Celsius. Therefore, the measurement sensors 13 can measure the field as close to the scull (head) as possible. The dependence of the measured magnetic field on the distance of the sensors to the brain current was calculated in article "A new generation of magnetoencephalography: Room temperature measurements using optically-pumped magnetometers", by E. Boto, et. al., NeuroImage 149 (2017) 404-414. FIG. 5a shows an analytical calculation model. A sphere with a radius of 10 cm is taken as the shape of the head. There is a local current element 41 at a depth d. A sensor system comprising sensor modules 27 is located at a distance h from the scalp 29. It is constructing a magnetic field radial projection map on a sphere of a corresponding radius. The maximum field value largely depends on d and h. Typical distances from the scalp to the sensors are 30 mm for SQUID, 6 mm for OPM and a distance in the range of 0.5 mm to 3 mm, or more specifically a distance in the range of 0.5 mm to 1.5 mm for the sensor module of the present invention. FIG. 5b shows the dependence of the maximum magnetic fields measured by these magnetometers on the depth of the current. FIG. 5c shows the ratio of fields measured by the magnetometers based on the Faraday material according to the present invention and OPM (lower curve), and measured by the magnetometers based on the Faraday material according to the present invention and SQUID (upper curve) as a function of depth. The magnetic field measured by the sensor module according to the present invention exceeds the value on SQUID sensors by 8 times and by 60% the value on OPM sensors for a source located at a depth of 2 cm. For more shallow sources the advantage is even greater. The magnetic field measured by the sensor module according to the present invention exceeds the value on the SQUID sensors by 18 times and by 2 times the value on the OPM sensors for a source at a depth of 1 cm.

The third main advantage of the proposed system is the ability to being able to operate in non-zero external magnetic fields, i.e., in a regular environment with ambient magnetic fields including the Earth's magnetic field. For instance, FIG. 3 illustrates a pack of sensors capable of measuring the field created by the brain activity. The measurement sensors measuring the total magnetic field, including the field from the brain and the external field, are close to the scalp 29. The reference sensor 31 is placed at a certain distance from the scalp 29 and the measurement sensors 13. In this example, the reference sensor is directed in parallel to the rest of the sensors, so it measures the same radial projection of the total magnetic field. However, the magnetic field created by the brain activity and as measured by the reference sensor 31 is much smaller than that measured by the measurement sensors 13 placed closer to the scalp due to the distance between magneto-optical films 15 of the reference sensor 31 and the measurement sensors 13. Thus, the magnetic fields created by neural activity in the brain can be obtained by specific processing or even by subtracting the reference signal obtained from the reference sensor 31 from the measurement signals obtained from the measurement sensors 13. In this example, this data processing or subtraction takes place in the data analysis system 37. For this purpose, the photodiode 17 or any other suitable light detector determines the brightness values of the light beams it has received and from these values it can determine how much the received light beam is rotated, i.e. the deflection angle, with respect to the originally emitted light beam by the light source. As the Verdet constant V for the Faraday material 23 and the used wavelength is known, the magnetic field value can now be determined by using the following equation: deflection angle=V×B. According to calculations similar to those given above, if the depth of the source of brain activity d is 1 cm and a distance h to the reference sensor is 2 cm, than the magnetic field created by the brain activity and as measured by the reference sensor 31 is approximately 8 times smaller than the field measured close to the scull. However, the distance between the measurement sensors 13 and the reference sensor 31 inside a given sensor module can be less than 2 cm. The distance of 2 cm is merely indicated for clarity and ease of calculation. The distance between the sensors 13 and the reference sensor is advantageously in the range of 0.1 cm to 5 cm, or more specifically between 0.5 cm to 3 cm.

In view of the above, according to one example, the present invention proposes a measurement system for building a magnetic field map of an object. The system comprises: a light source arrangement for emitting a plurality of light signals, a respective light signal being configured to travel in the measurement system along a respective optical path. The system also comprises a plurality of measurement sensors. Each measurement sensor is configured to receive the respective light signal along the respective optical path. The plurality of measurement sensors share a first magneto-optical layer comprising at least a first Faraday material layer and a first light reflector for reflecting the plurality of light signals travelled through the first Faraday material layer in a first direction back to the first Faraday material layer in a second, opposite direction. The first magneto-optical layer is configured to rotate polarization of the plurality of light signals in the presence of a magnetic field such that the amount of rotation depends on the strength of the magnetic field. The system further comprises one or more reference sensors placed at a predetermined distance from the plurality of measurement sensors. Each reference sensor is configured to receive the respective light signal along the respective optical path. The one or more reference sensors comprise a second magneto-optical layer comprising at least a second Faraday material layer and a second light reflector for reflecting the respective light signal travelled through the second Faraday material layer in a first direction back to the second Faraday material layer in a second, opposite direction. The second magneto-optical layer is configured to rotate polarization of the respective light signal in the presence of a magnetic field such that the amount of rotation depends on the strength of the magnetic field. Moreover, the system comprises one or more light detectors for receiving the light signals travelled in the second direction from the plurality of measurement sensors and the one or more reference sensors to determine light intensity values and an interference pattern of the received light signals to thereby determine polarization rotation values of the received light signals with respect to the emitted plurality of light signals for building the magnetic field map.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims. Further variants may be obtained by combining the teachings of any of the designs explained above.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A measurement system for building a magnetic field map of an object, the system comprising:
    a light source arrangement for emitting a plurality of light beams, a respective light beam being configured to travel in the measurement system along a respective optical path;
    a plurality of measurement sensors, a respective measurement sensor being configured to receive the respective light beam along the respective optical path, the plurality of measurement sensors sharing a first magneto-optical layer comprising at least a first Faraday material layer and a first light reflector for reflecting the plurality of light beams travelled through the first Faraday material layer in a first direction back to the first Faraday material layer in a second, opposite direction, the first magneto-optical layer being configured to rotate polarization of the plurality of light beams in the presence of a first magnetic field such that the amount of rotation depends on the strength of the first magnetic field;
    one or more reference sensors arranged at a given distance from the plurality of measurement sensors, a respective reference sensor being configured to receive the respective light beam along the respective optical path, the one or more reference sensors comprising a second magneto-optical layer comprising at least a second Faraday material layer and a second light reflector for reflecting the respective light beam travelled through the second Faraday material layer in a first direction back to the second Faraday material layer in a second, opposite direction, the second magneto-optical layer being configured to rotate polarization of the respective light beam in the presence of a second magnetic field such that the amount of rotation depends on the strength of the second magnetic field; and
    one or more light detectors for receiving the light beams travelled in the second direction from the plurality of measurement sensors and the one or more reference sensors to determine light intensity values of the received light beams to thereby determine polarization rotation values of the received light beams with respect to the emitted plurality of light beams for building the magnetic field map.

2. The system according to claim 1, wherein the system further comprises a plurality of optical fibers for forming the optical paths, a respective optical fiber comprising a first end and a second end such that the respective light beam is configured to travel between the first and second ends, and wherein the measurement and reference sensors are configured to receive the light beams from the second ends of the optical fibers.

3. The system according to claim 1, wherein the light source arrangement comprises a light source for generating and emitting a plurality of light source beams, and a beam splitter for dividing the light source beams into the plurality of light beams.

4. The system according to claim 1, wherein the first magneto-optical layer further comprises a first polarization conversion layer, and the second magneto-optical layer further comprises a second polarization conversion layer, wherein the first and second polarization conversion layers are configured to convert two orthogonal polarizations into right-handed and left-handed circular polarizations.

5. The system according to claim 4, wherein the first and second polarization conversion layers are quarter-wave plates.

6. The system according to claim 1, wherein the first Faraday material layer is characterized by a first Verdet constant for a given wavelength, and the second Faraday material layer is characterized by a second Verdet constant for a given wavelength, wherein the first and second Verdet constants have a value greater than $10^7°$/Tm for a wavelength in the range of 400 nm to 1100 nm.

7. The system according to claim 1, wherein the first Faraday material layer and/or the second Faraday material layer is/are selected from a non-limiting list comprising yttrium iron garnet, $Tb^{+3}$ doped paramagnetic glass, gallium gadolinium garnet, cobalt-zinc ferrite, bismuth-dysprosium ferrite, silicate mineral, chiral hydrocarbon polymer, magnetite nanoparticles, and any combination thereof.

8. The system according to claim 1, wherein the system further comprises a plurality of optical circulators for redirecting the plurality of light beams, wherein the respective optical path comprises a respective optical circulator.

9. The system according to claim 1, wherein the system comprises a plurality of polarizers for converting the plurality of light beams to a linearly polarized light beams, wherein the respective optical path comprises a respective polarizer.

10. The system according to claim 1, wherein the system comprises a plurality of optical splices for splicing the polarization of the plurality of light beams into two different polarizations, and for combining different rotated polarizations of the plurality of light beams travelling in the second direction, wherein the respective optical path comprises a respective optical splice.

11. The system according to claim 1, wherein the measurement and reference sensors comprises a plurality of collimators for narrowing the plurality of light beams, wherein a respective measurement and reference sensor comprises a respective collimator.

12. The system according to claim 1, wherein the one or more light detectors are photodiodes.

13. The system according to claim 1, wherein the distance between the plurality of measurement sensors and the one or more reference sensors is in the range of 0.1 cm to 5 cm.

14. The system according to claim 1, wherein the system is configured to subtract a respective light beam received from the one or more reference sensors travelled in the second direction from a respective light beam received from the plurality of measurement sensors travelled in the second direction prior to determining the light intensity values of the received light beams.

15. The system according to claim 1, wherein the system further comprises an analog-to-digital converter for digitizing light detector output signals from the one or more light detectors.

16. The system according to claim 1, wherein the object is a human or animal brain.

17. The system according to claim 1, wherein the first Faraday material layer is made of the same material as the second Faraday material layer.

18. The system according to claim 1, wherein the first and second magneto-optical layers have a thickness in the range of 10 μm to 500 μm.

19. A method of building a magnetic field map of an object in a measurement system, the system comprising:
- a light source arrangement for generating a plurality of light beams, a respective light beam being configured to travel in the measurement system along a respective optical path;
- a plurality of measurement sensors, a respective measurement sensor being configured to receive the respective light beam along the respective optical path, the plurality of measurement sensors sharing a first magneto-optical layer comprising at least a first Faraday material layer and a first light reflector for reflecting the plurality of lights beams travelled through the first Faraday material layer in a first direction back to the first Faraday material layer in a second, opposite direction, the first magneto-optical layer being configured to rotate polarization of the plurality of light beams in the presence of a first magnetic field such that the amount of rotation depends on the strength of the first magnetic field;
- one or more reference sensors arranged at a given distance from the plurality of measurement sensors, a respective reference sensor being configured to receive the respective light beam along the respective optical path, the one or more reference sensors comprising a second magneto-optical layer comprising at least a second Faraday material layer and a second light reflector for reflecting the respective light beams travelled through the second Faraday material layer in a first direction back to the second Faraday material layer in a second, opposite direction, the second magneto-optical layer being configured to rotate polarization of the respective light beam in the presence of a second magnetic field such that the amount of rotation depends on the strength of the second magnetic field; and
- one or more light detectors for receiving the light beams travelled in the second direction from the plurality of measurement sensors and the one or more reference sensors to determine light intensity values of the received light beams to thereby determine polarization rotation values of the received light beams for building the magnetic field map, the method comprising the steps of:
- the light source arrangement emitting the plurality of light beams; and
- the one or more light detectors determining the light intensity values of the received light beams to thereby determine polarization rotation values of the received light beams with respect to the emitted plurality of light beams for building the magnetic field map.

* * * * *